United States Patent
Lattner et al.

(10) Patent No.: US 6,838,587 B2
(45) Date of Patent: Jan. 4, 2005

(54) METHOD OF REMOVING OXYGENATE CONTAMINANTS FROM AN OLEFIN STREAM

(75) Inventors: James R. Lattner, Seabrook, TX (US); David R. Lumgair, Jr., Craddockville, VA (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 279 days.

(21) Appl. No.: 10/126,390

(22) Filed: Apr. 19, 2002

(65) Prior Publication Data

US 2003/0199722 A1 Oct. 23, 2003

(51) Int. Cl.$^7$ .............................. C07C 7/04; C07C 7/10
(52) U.S. Cl. ...................... 585/807; 585/809; 585/833; 585/639; 585/864
(58) Field of Search ................................ 585/807, 809, 585/833, 864, 639

(56) References Cited

U.S. PATENT DOCUMENTS

| | | | |
|---|---|---|---|
| 2,238,490 A | * | 4/1941 | Rudolph ...................... 95/176 |
| 2,409,250 A | * | 10/1946 | Cannon et al. ............... 95/193 |
| 3,265,593 A | * | 8/1966 | Leis et al. ..................... 203/60 |
| 3,663,641 A | * | 5/1972 | Hanson ....................... 585/868 |
| 4,474,647 A | | 10/1984 | Asselineau et al. ........... 203/49 |
| 4,499,327 A | | 2/1985 | Kaiser ........................ 585/640 |
| 5,090,977 A | | 2/1992 | Strack et al. ................... 62/23 |
| 5,336,836 A | * | 8/1994 | Mueller et al. ............. 585/824 |
| 5,720,929 A | | 2/1998 | Minkkinen et al. ......... 422/194 |
| 5,914,433 A | | 6/1999 | Marker ........................ 585/313 |
| 6,037,516 A | * | 3/2000 | Morford et al. ............ 585/836 |
| 6,121,504 A | | 9/2000 | Kuechler et al. ........... 585/640 |
| 6,559,248 B2 | * | 5/2003 | Hendriksen et al. .......... 526/77 |

FOREIGN PATENT DOCUMENTS

| EP | 0 060 103 | 4/1985 | ............. C07C/1/20 |
|---|---|---|---|
| JP | 08 269 470 | 10/1995 | |

OTHER PUBLICATIONS

Eng, Curtis N., et al, "Integration of the UOP/HYDRO MTO Process into Ethylene Plants," *10th Ethylene Producers' Conference*, 1998, pp. 54–85.

* cited by examiner

*Primary Examiner*—Walter D. Griffin
*Assistant Examiner*—Tam M. Nguyen

(57) ABSTRACT

This invention is directed to a method of removing acetaldehyde, $CO_2$ and/or water from an ethylene and/or propylene containing stream. In this invention, acetaldehyde and $C_4+$ olefins are substantially removed from the ethylene and/or propylene containing stream. The stream is then acid gas treated. The ethylene and/or propylene streams which are separated and recovered according to this invention can be further processed, for example, to make polymers such as polyethylene and polypropylene.

45 Claims, 1 Drawing Sheet

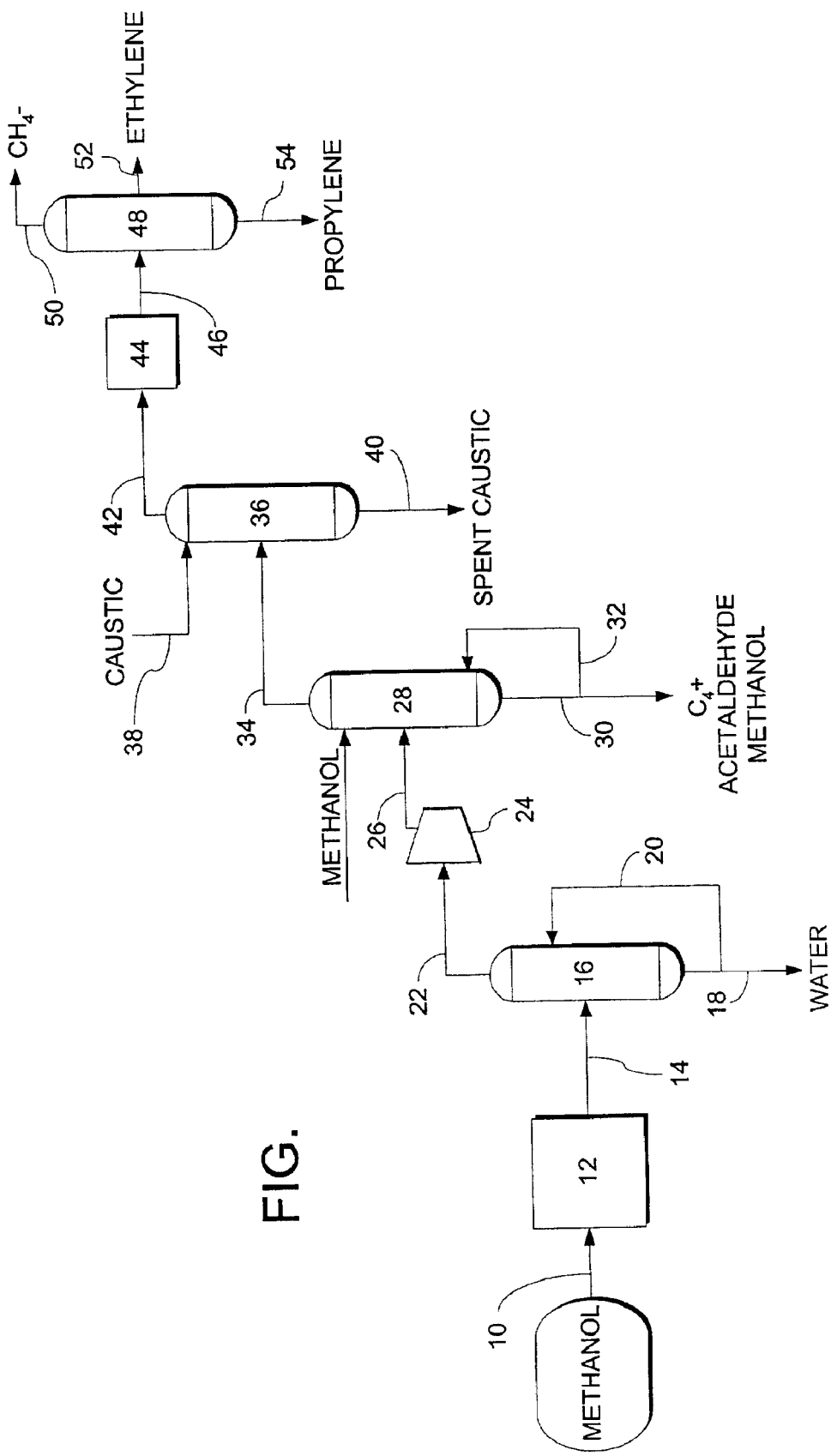

METHOD OF REMOVING OXYGENATE CONTAMINANTS FROM AN OLEFIN STREAM

FIELD OF THE INVENTION

This invention is directed to a method of removing oxygenated contaminants from an olefin stream. In particular, this invention is directed to a method of removing acetaldehyde, $CO_2$ and/or water from an ethylene and/or propylene containing stream.

BACKGROUND OF THE INVENTION

Olefins, particularly $C_2$ and $C_3$ olefins, are desirable as a feed source for making derivative products such as oligomers, e.g., higher olefins, and polymers such as polyethylene and polypropylene. Olefin feed sources have traditionally been produced by cracking petroleum feedstocks.

U.S. Pat. No. 5,090,977 discloses a method of making olefins by steam cracking. The method includes separating the olefin product into methane, hydrogen, ethane, ethylene, propylene and $C_5$+ streams. The disclosed separation preferentially produces propylene, and no propane, butane, butene, or butadiene streams are produced.

Oxygenate feed stocks, however, are becoming an alternative to petroleum feed stocks for making olefins, particularly large quantities of ethylene and propylene for the production of higher olefins and plastic materials. In general, the olefins are formed by contacting the oxygenate components with a molecular sieve catalyst to catalytically convert the oxygenates to olefins.

For example, U.S. Pat. No. 4,499,327, discloses a process for making olefins from methanol using any of a variety of silicoaluminophosphate (SAPO) molecular sieve catalysts. The process is carried out at a temperature between 300° C. and 500° C., a pressure between 0.1 atmosphere to 100 atmospheres, and a weight hourly space velocity (WHSV) of between 0.1 and 40 $hr^{-1}$. The process is highly selective for making ethylene and propylene.

U.S. Pat. No. 6,121,504 also discloses a method of making olefin product from oxygenate feed using molecular sieve catalysts. Water and other unwanted by-products are removed from the olefin product by contacting with a quench medium. After contacting with the quench medium, a light product fraction is obtained which comprises the desired olefins, but also includes dimethyl ether, methane, CO, $CO_2$, ethane, propane, and other minor components such as water and unreacted oxygenate feedstock.

In order to further process olefins, it is often necessary to reduce or remove undesirable by-products that are present in the olefin composition. For example, U.S. Pat. No. 4,474,647 discloses that dimethyl ether can adversely impact the oligomerization of certain olefins. The patent describes a process for removing dimethyl ether from a $C_4$ and/or $C_5$ olefin stream using distillation. The stream is distilled and separated into an overhead and a bottoms stream. The overhead stream contains dimethyl ether, water, and various hydrocarbons, and the bottoms stream contains purified olefins.

U.S. Pat. No. 5,914,433 discloses a method of making an olefin composition, and a system for removing non-olefin by-products such as $CO_2$. A dewatered olefin composition is washed with caustic to remove $CO_2$, and the washed olefin composition is dried to reduce water added as a result of the caustic wash.

U.S. Pat. No. 5,720,929 discloses a process which includes making isobutylene from isobutane. The isobutylene is cooled and water is stripped from the product. Additional water is removed by washing the product with methanol.

Eng et al., "Integration of the UOP/HYDRO MTO Process into Ethylene Plants," 10th Ethylene Producers' Conference, 1998, disclose a flow scheme for making an olefin composition from methanol. The flow scheme shows a deethanizer-first flow process.

EP-B1-0 060 103 discloses a process for extracting dimethyl ether from a vapor stream containing ethylene and propylene using a methanol wash system. The methanol wash removes a substantial amount of the dimethyl ether, but also removes a significant amount of the ethylene and propylene.

Additional methods of removing undesirable components from olefin streams are sought. In particular, methods for removing oxygenated hydrocarbons, particularly acetaldehyde, as well as $CO_2$ and water down to the ppm level in olefin product streams, and without removing significant amounts of olefin, are sought.

SUMMARY OF THE INVENTION

This invention provides a method for removing oxygenated components such as acetaldehyde, $CO_2$ and/or water from an olefin stream. It is desirable to remove such oxygenated components, since they may poison catalysts that are used to further process olefin composition. In addition, the presence of certain oxygenated compounds, such as acetaldehyde, can cause fouling in other olefin purification units, e.g., acid gas treating units.

The invention provides, in one embodiment, a method of treating an ethylene and/or propylene containing stream. The method comprises providing an olefin stream containing ethylene, propylene, $C_4$+ olefins and acetaldehyde. The olefin stream is separated into a first fraction and a second fraction, wherein the first fraction comprises at least a majority of the ethylene and/or propylene present in the olefin stream, and the second fraction comprises at least a majority of the $C_4$+ olefins and acetaldehyde present in the olefin stream. The first fraction is then acid gas treated.

In another embodiment, the olefin stream is separated by distillation. Preferably, the distillation is extractive distillation using an extractant. The preferred extractant is a polar composition having an average boiling point of at least 100° F. (38° C.) at 1 atm. Methanol is one type of preferred extractant.

In another embodiment, the invention provides a method of treating an ethylene and/or propylene containing stream made from an oxygenate to olefin process. The method comprises contacting oxygenate with a molecular sieve catalyst to form an olefin stream comprising ethylene, propylene, and acetaldehyde. The olefin stream is separated into a first fraction and a second fraction, wherein the first fraction comprises at least a majority of the ethylene and/or propylene present in the olefin stream, and the second fraction comprises at least a majority of the acetaldehyde present in the olefin stream. The first fraction is then acid gas treated.

There is provided, in another embodiment, a method of treating an ethylene containing stream. The method comprises providing an olefin stream containing ethylene, propylene, $C_4$+ olefins and acetaldehyde. The olefin stream is separated into a first fraction and a second fraction, wherein the first fraction comprises at least a majority of the ethylene present in the olefin stream, and the second fraction comprises at least a majority of the propylene, the $C_4+$ olefin, and the acetaldehyde present in the olefin stream. The first fraction is then acid gas treated.

In yet another embodiment, there is provided a method of treating an ethylene and propylene containing stream. The method comprises providing an olefin stream containing ethylene, propylene, $C_4+$ olefins and acetaldehyde. The olefin stream is separated into a first fraction and a second fraction, wherein the first fraction comprises at least a majority of the ethylene and propylene present in the olefin stream and the second fraction comprises at least a majority of the $C_4+$ olefin and acetaldehyde present in the olefin stream. The first fraction is then acid gas treated.

In another embodiment, the provided olefin stream further comprises $CO_2$, and the first fraction further contains at least a majority of the $CO_2$ in the provided olefin stream. It is further desirable to acid gas treat the first fraction to remove entrained $CO_2$. As one example, acid gas treating the first fraction comprises contacting the first fraction with caustic.

BRIEF DESCRIPTION OF THE DRAWING

One embodiment of invention is shown in the attached FIGURE, which is a flow diagram showing one particular embodiment for separating acetaldehyde and $C_4+$ olefins from an ethylene and/or propylene containing stream.

DETAILED DESCRIPTION OF THE INVENTION

This invention provides a method of removing oxygenate contaminants, for example acetaldehyde, $CO_2$ and/or water, from an olefin stream. In general, the method comprises providing an olefin stream containing ethylene, propylene, and acetaldehyde, then removing a majority of the acetaldehyde present in the olefin stream. The olefin stream can come from any conventional source, and can include other components such as $CO_2$, water and/or $C_4+$ olefins.

This invention is particularly beneficial in removing oxygenate contaminants from olefin streams made in oxygenate to olefins processes. In these streams, acetaldehyde, $CO_2$ and water can be present in relatively high concentrations, and their presence can cause problems in further processing ethylene and propylene from these streams. For example, these contaminants can poison polyethylene and polypropylene forming catalysts, and the presence of acetaldehyde can also be problematic in the removal of entrained acid gases such as $CO_2$.

In one embodiment of the invention, the olefin stream that is provided comprises not greater than about 5 wt % acetaldehyde, preferably not greater than about 2 wt % acetaldehyde, and more preferably not greater than about 1 wt % acetaldehyde. Of course, for acetaldehyde to be removed from the olefin stream, some measurable amount must be present. In one embodiment, the provided olefin stream will contain at least about 100 wppm acetaldehyde; in another, at least about 500 wppm acetaldehyde; and in yet another, at least about 1000 wppm acetaldehyde.

In another embodiment, the olefin stream that is provided comprises at least about 25 wt % ethylene. Preferably, the provided olefin stream comprises from about 25 wt % ethylene to about 75 wt % ethylene, more preferably from about 30 wt % to about 60 wt %, and most preferably from about 35 wt % to about 50 wt % propylene.

In another embodiment, the olefin stream that is provided also comprises at least about 20 wt % propylene. Preferably, the provided olefin stream comprises from about 20 wt % propylene to about 70 wt % propylene, more preferably from about 25 wt % to about 50 wt % propylene, and most preferably from about 30 wt % to about 40 wt % propylene.

It is desirable that the provided olefin stream contain a relatively low concentration of ethane, preferably a lower concentration of ethane than propane. Preferably, the olefin stream comprises not greater than about 4 wt % ethane, more preferably not greater than about 3 wt % ethane, and most preferably not greater than about 2 wt % ethane.

It is also desirable that the provided olefin stream contain a relatively low concentration of propane. Preferably, the olefin stream comprises not greater than about 5 wt % propane, more preferably not greater than about 4 wt % propane, and most preferably not greater than about 3 wt % propane.

In another embodiment of the invention, the provided olefin stream contains both ethylene and propylene. Desirably, the olefin stream contains at least about 50 wt % ethylene and propylene. Preferably, the olefin stream contains from about 50 wt % to about 95 wt % ethylene and propylene, more preferably from about 55 wt % to about 90 wt % ethylene and propylene, and most preferably from about 60 wt % to about 85 wt % ethylene and propylene.

It is desirable in this invention that the provided olefin stream contain not greater than about 15,000 wppm water. Preferably the olefin stream contains not greater than about 10,000 wppm water, more preferably not greater than 5,000 wppm water, and most preferably not greater than about 1,000 wppm water.

It is not necessary in this invention that the olefin stream be completely dry. That is, the olefin stream can contain some water. The benefit of the olefin stream containing some amount of water is that additional and/or complex drying equipment will not be needed before separating the acetaldehyde from the olefin stream. Preferably, the olefin stream contains at least about 10 wppm water, more preferably at least about 100 wppm water, and most preferably at least about 200 wppm water.

In another embodiment, the olefin stream that is provided comprises not greater than about 40 wt % $C_4+$ olefins. Preferably the provided olefin stream comprises not greater than about 30 wt % $C_4+$ olefins, more preferably not greater than about 20 wt % $C_4+$ olefins.

Following separation of at least a majority (i.e., at least 50%) of the acetaldehyde and $C_4+$ olefins present in the olefin stream, ethylene and/or propylene containing streams are recovered which contain at least a majority (i.e., at least 50%) of the ethylene and/or propylene in the provided olefin stream. These ethylene and/or propylene containing streams require little if any further treatment prior to making polymers or other derivative products.

In one embodiment of the invention, propylene is separated along with the acetaldehyde and $C_4+$ olefins. In this embodiment, an ethylene containing stream is separately recovered and treated or further processed.

In another embodiment of the invention, ethylene and propylene are recovered in a first fraction, and then separated from one another. The streams can be treated, if desired, before or after separation. It is preferable, however, to acid gas treat (i.e., remove acid gases such as $CO_2$), then separate the components into an ethylene stream and a propylene stream. Each stream is then further processed.

In one embodiment, for example, the recovered ethylene and/or propylene steams comprise not greater than about 100 wppm acetaldehyde. Preferably, the recovered ethylene and/or propylene steams comprise not greater than about 50 wppm acetaldehyde, more preferably not greater than about 5 wppm acetaldehyde, and most preferably not greater than about 1 wppm acetaldehyde.

In another embodiment of the invention, ethylene is recovered in a first fraction which contains at least a majority of the ethylene present in the provided olefin stream. Preferably the recovered ethylene stream comprises at least about 70 wt % ethylene, more preferably at least about 80 wt % ethylene, and most preferably at least about 90 wt % ethylene, based on the total weight of the stream.

When ethylene and propylene are recovered together in one stream, the overhead stream contains at least a majority of the ethylene and propylene present in the provided olefin stream. Preferably the recovered ethylene and propylene stream comprises at least about 70 wt % ethylene and propylene, more preferably at least about 80 wt % ethylene and propylene, and most preferably at least about 90 wt % ethylene and propylene, based on the total weight of the stream.

It is also desirable that the recovered ethylene and/or propylene steams comprise not greater than about 0.1 wt % $C_4+$ olefins. Preferably, the recovered ethylene and/or propylene steams comprise not greater than about 0.05 wt % $C_4+$ olefins, and more preferably not greater than about 0.01 wt % $C_4+$ olefins, based on the total weight of the stream.

Removal of acetaldehyde from an olefin stream can be accomplished by any conventional means capable of removing such by-product to the appropriate level. Conventional distillation techniques are particularly desirable methods, and temperatures and pressures effective for separating acetaldehyde and $C_4+$ olefins from ethylene and/or propylene according to boiling point are used.

In order to obtain a particularly high degree of separation between acetaldehyde and $C_4+$ olefins from ethylene and/or propylene, extractive distillation can be optionally used. Extractive distillation differs from conventional distillation to the extent that the ethylene and/or propylene is distilled from the acetaldehyde and $C_4+$ olefins using an extractant to aid the distillation process.

Extractive distillation is carried out using a vessel or tower having internal packing or trays that creates a temperature difference from top to bottom of the tower. The upper portion of the tower is the cooler portion, and higher volatile components in the feed exit from the top of the tower.

An extractant or solvent is added to the extractive distillation vessel or tower so as to enhance or suppress the volatility of the oxygenate contaminant, e.g., acetaldehyde, relative to the olefin. This makes it easier to distill the oxygenate from the olefin, resulting in removal of the oxygenate to very low levels.

Extractants which can be used in this invention are liquids at 1 atm. These extractants also desirably have an average boiling point of at least 100° F. (38° C.), preferably at least 120° F. (49° C.), and more preferably at least 150° F. (66° C.). Average boiling point, as defined herein, takes into account the boiling point of each compound in the extractant on a weight average basis. For example, an extractant containing 90 wt. % of a compound having a boiling point of 100 degrees and 10 wt. % of a compound having a boiling point of 200 degrees would have an average boiling point of 110 degrees.

The extractants are also desirably polar compositions. Such compositions preferably contain compounds such as water, monohydric alcohols, polyhydric alcohols, or mixtures thereof. Preferred monohydric alcohols include methanol, ethanol and propanol. Preferred polyhydric alcohols include glycols. Preferred glycols include ethylene glycol and tri-ethylene glycol. It is desirable that the extractant contain at least about 75 wt. % water, monohydric alcohol, and/or polyhydric alcohol, preferably at least about 85 wt. %, more preferably at least about 90 wt. %, and most preferably at least about 95 wt. %. Methanol is most preferred as the extractant in this invention.

The extractive distillation process is particularly effective for removing very low concentrations of oxygenate contaminants present in an olefin stream. In one embodiment of the invention, extractant is added at an upper region of an extractive distillation column, and the olefin containing acetaldehyde is added at a side region of the column. Separated ethylene and/or propylene is recovered from the column in a first fraction, preferably from an upper portion of the column, and the separated $C_4+$ and acetaldehyde is recovered in a second fraction, preferably from a lower portion of the column. A majority of the added extractant (i.e., at least 50% of the amount added to the column) is also recovered from a lower portion of the column, preferably along with the recovered $C_4+$ and acetaldehyde.

In one embodiment of the invention, the separated $C_4+$ olefin and acetaldehyde stream comprises at least a majority (i.e., at least 50%) of the acetaldehyde and $C_4+$ olefins present in the provided olefin stream. Preferably, the stream comprises at least about 5 wt % $C_4+$ olefins, more preferably about 10 wt % $C_4+$ olefins, most preferably about 15 wt % $C_4+$ olefins, based on the total weight of the stream. The $C_4+$ containing stream also includes acetaldehyde. In one embodiment, the stream comprises at least about 1,000 wppm acetaldehyde; in another, at least about 1,500 wppm; and in yet another, at least about 2,000 wppm, based on the total weight of the stream.

In another embodiment of the invention, the stream containing the separated $C_4+$ and acetaldehyde product includes extractant. Preferably the stream comprises at least about 50 wt % extractant, more preferably at least about 60 wt %, and most preferably at least about 70 wt %. Preferably the extractant is methanol.

Although the olefin stream can come from any conventional source which contains acetaldehyde, the invention is particularly suited to removing acetaldehyde from olefin streams made from an oxygenate to olefin process. In one embodiment of this invention, an olefin stream containing acetaldehyde is obtained by contacting oxygenate feedstock with a molecular sieve catalyst.

In a preferred embodiment of the process of the invention, the oxygenate feedstock contains one or more oxygenates, more specifically, one or more organic compound(s) containing at least one oxygen atom. In the most preferred embodiment of the process of invention, the oxygenate in the feedstock is one or more alcohol(s), preferably aliphatic alcohol(s) where the aliphatic moiety of the alcohol(s) has from 1 to 20 carbon atoms, preferably from 1 to 10 carbon atoms, and most preferably from 1 to 4 carbon atoms. The alcohols useful as feedstock in the process of the invention include lower straight and branched chain aliphatic alcohols and their unsaturated counterparts. Non-limiting examples of oxygenates include methanol, ethanol, n-propanol, isopropanol, methyl ethyl ether, dimethyl ether, diethyl ether, di-isopropyl ether, formaldehyde, dimethyl carbonate, dimethyl ketone, acetic acid, and mixtures thereof. In the most preferred embodiment, the feedstock is selected from one or more of methanol, ethanol, dimethyl ether, diethyl ether or a combination thereof, more preferably methanol and dimethyl ether, and most preferably methanol.

The feedstock, in one embodiment, contains one or more diluent(s), typically used to reduce the concentration of the feedstock, and are generally non-reactive to the feedstock or molecular sieve catalyst composition. Non-limiting examples of diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. The most preferred diluents are water and nitrogen, with water being particularly preferred.

The diluent is either added directly to a feedstock entering into a reactor or added directly into a reactor, or added with a molecular sieve catalyst composition. In one embodiment, the amount of diluent in the feedstock is in the range of from about 1 to about 99 mole percent based on the total number of moles of the feedstock and diluent, preferably from about 1 to 80 mole percent, more preferably from about 5 to about 50, most preferably from about 5 to about 25. In one embodiment, other hydrocarbons are added to a feedstock either directly or indirectly, and include olefin(s), paraffin(s), aromatic(s) (see for example U.S. Pat. No. 4,677,242, addition of aromatics) or mixtures thereof, preferably propylene, butylene, pentylene, and other hydrocarbons having 4 or more carbon atoms, or mixtures thereof.

Molecular sieves capable of converting an oxygenate to an olefin compound include zeolite as well as non-zeolite molecular sieves, and are of the large, medium or small pore type. Non-limiting examples of these molecular sieves are the small pore molecular sieves, AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, THO, and substituted forms thereof; the medium pore molecular sieves, AFO, AEL, EUO, HEU, FER, MEL, MFI, MTW, MTT, TON, and substituted forms thereof; and the large pore molecular sieves, EMT, FAU, and substituted forms thereof. Other molecular sieves include ANA, BEA, CFI, CLO, DON, GIS, LTL, MER, MOR, MWW and SOD. Non-limiting examples of the preferred molecular sieves, particularly for converting an oxygenate containing feedstock into olefin(s), include AEL, AFY, BEA, CHA, EDI, FAU, FER, GIS, LTA, LTL, MER, MFI, MOR, MTT, MWW, TAM and TON. In one preferred embodiment, the molecular sieve of the invention has an AEI topology or a CHA topology, or a combination thereof, most preferably a CHA topology.

Molecular sieve materials all have 3-dimensional, four-connected framework structure of corner-sharing $TO_4$ tetrahedra, where T is any tetrahedrally coordinated cation. These molecular sieves are typically described in terms of the size of the ring that defines a pore, where the size is based on the number of T atoms in the ring. Other framework-type characteristics include the arrangement of rings that form a cage, and when present, the dimension of channels, and the spaces between the cages. See van Bekkum, et al., *Introduction to Zeolite Science and Practice, Second Completely Revised and Expanded Edition*, Volume 137, pages 1–67, Elsevier Science, B. V., Amsterdam, Netherlands (2001).

The small, medium and large pore molecular sieves have from a 4-ring to a 12-ring or greater framework-type. In a preferred embodiment, the molecular sieves have 8-, 10- or 12-ring structures or larger and an average pore size in the range of from about 3 Å to 15 Å. In the most preferred embodiment, the molecular sieves of the invention, preferably silicoaluminophosphate molecular sieves, have 8-rings and an average pore size less than about 5 Å, preferably in the range of from 3 Å to about 5 Å, more preferably from 3 Å to about 4.5 Å, and most preferably from 3.5 Å to about 4.2 Å.

Molecular sieves, particularly zeolitic and zeolitic-type molecular sieves, preferably have a molecular framework of one, preferably two or more corner-sharing $[TO_4]$ tetrahedral units, more preferably, two or more $[SiO_4]$, $[AlO_4]$ and/or $[PO_4]$ tetrahedral units, and most preferably $[SiO_4]$, $[AlO_4]$ and $[PO_4]$ tetrahedral units. These silicon, aluminum, and phosphorous based molecular sieves and metal containing silicon, aluminum and phosphorous based molecular sieves have been described in detail in numerous publications including for example, U.S. Pat. No. 4,567,029 (MeAPO where Me is Mg, Mn, Zn, or Co), U.S. Pat. No. 4,440,871 (SAPO), European Patent Application EP-A-0 159 624 (ELAPSO where El is As, Be, B, Cr, Co, Ga, Ge, Fe, Li, Mg, Mn, Ti or Zn), U.S. Pat. No. 4,554,143 (FeAPO), U.S. Pat. No. 4,822,478, 4,683,217, 4,744,885 (FeAPSO), EP-A-0 158 975 and U.S. Pat. No. 4,935,216 (ZNAPSO, EP-A-0 161 489 (CoAPSO), EP-A-0 158 976 (ELAPO, where EL is Co, Fe, Mg, Mn, Ti or Zn), U.S. Pat. No. 4,310,440 ($AlPO_4$), EP-A-0 158 350 (SENAPSO), U.S. Pat. No. 4,973,460 (LiAPSO), U.S. Pat. No. 4,789,535 (LiAPO), U.S. Pat. No. 4,992,250 (GeAPSO), U.S. Pat. No. 4,888,167 (GeAPO), U.S. Pat. No. 5,057,295 (BAPSO), U.S. Pat. No. 4,738,837 (CrAPSO), U.S. Pat. Nos. 4,759,919, and 4,851,106 (CrAPO), U.S. Pat. Nos. 4,758,419, 4,882,038, 5,434,326 and 5,478,787 (MgAPSO), U.S. Pat. No. 4,554,143 (FeAPO), U.S. Pat. No. 4,894,213 (AsAPSO), U.S. Pat. No. 4,913,888 (AsAPO), U.S. Pat. Nos. 4,686,092, 4,846,956 and 4,793,833 (MnAPSO), U.S. Pat. Nos. 5,345,011 and 6,156,931 (MnAPO), U.S. Pat. No. 4,737,353 (BeAPSO), U.S. Pat. No. 4,940,570 (BeAPO), U.S. Pat. Nos. 4,801,309, 4,684,617 and 4,880,520 (TiAPSO), U.S. Pat. Nos. 4,500,651, 4,551,236 and 4,605,492 (TiAPO), U.S. Pat. No. 4,824,554, 4,744,970 (CoAPSO), U.S. Pat. No. 4,735,806 (GaAPSO) EP-A-0 293 937 (QAPSO, where Q is framework oxide unit $[QO_2]$), as well as U.S. Pat. Nos. 4,567,029, 4,686,093, 4,781,814, 4,793,984, 4,801,364, 4,853,197, 4,917,876, 4,952,384, 4,956,164, 4,956,165, 4,973,785, 5,241,093, 5,493,066 and 5,675,050, all of which are herein fully incorporated by reference.

Other molecular sieves include those described in EP-0 888 187 B1 (microporous crystalline metallophosphates, $SAPO_4$ (UIO-6)), U.S. Pat. No. 6,004,898 (molecular sieve and an alkaline earth metal), U.S. patent application Ser. No. 09/511,943 filed Feb. 24, 2000 (integrated hydrocarbon cocatalyst), PCT WO 01/64340 published Sep. 7, 2001 (thorium containing molecular sieve), and R. Szostak, Handbook of Molecular Sieves, Van Nostrand Reinhold, New York, N.Y. (1992), which are all herein fully incorporated by reference.

The more preferred silicon, aluminum and/or phosphorous containing molecular sieves, and aluminum, phosphorous, and optionally silicon, containing molecular sieves include aluminophosphate (ALPO) molecular sieves and silicoaluminophosphate (SAPO) molecular sieves and substituted, preferably metal substituted, ALPO and SAPO molecular sieves. The most preferred molecular sieves are SAPO molecular sieves, and metal substituted SAPO molecular sieves. In an embodiment, the metal is an alkali metal of Group IA of the Periodic Table of Elements, an alkaline earth metal of Group IIA of the Periodic Table of Elements, a rare earth metal of Group IIIB, including the Lanthanides: lanthanum, cerium, praseodymium, neodymium, samarium, europium, gadolinium, terbium, dysprosium, holmium, erbium, thulium, ytterbium and lutetium; and scandium or yttrium of the Periodic Table of Elements, a transition metal of Groups IVB, VB, VIB, VIIB, VIIIB, and IB of the Periodic Table of Elements, or mixtures of any of these metal species. In one preferred embodiment, the metal is selected from the group consisting of Co, Cr, Cu, Fe, Ga, Ge, Mg, Mn, Ni, Sn, Ti, Zn and Zr, and mixtures thereof. In another preferred embodiment, these metal atoms discussed above are inserted into the framework of a molecular sieve through a tetrahedral unit, such as [MeO$_2$], and carry a net charge depending on the valence state of the metal substituent. For example, in one embodiment, when the metal substituent has a valence state of +2, +3, +4, +5, or +6, the net charge of the tetrahedral unit is between −2 and +2.

In one embodiment, the molecular sieve, as described in many of the U.S. Patents mentioned above, is represented by the empirical formula, on an anhydrous basis:

$$mR:(M_xAl_yP_z)O_2$$

wherein R represents at least one templating agent, preferably an organic templating agent; m is the number of moles of R per mole of $(M_xAl_yP_y)O_2$ and m has a value from 0 to 1, preferably 0 to 0.5, and most preferably from 0 to 0.3; x, y, and z represent the mole fraction of Al, P and M as tetrahedral oxides, where M is a metal selected from one of Group IA, IIA, IB, IIIB, IVB, VB, VIB, VIIB, VIIIB and Lanthanide's of the Periodic Table of Elements, preferably M is selected from one of the group consisting of Co, Cr, Cu, Fe, Ga, Ge, Mg, Mn, Ni, Sn, Ti, Zn and Zr. In an embodiment, m is greater than or equal to 0.2, and x, y and z are greater than or equal to 0.01.

In another embodiment, m is greater than 0.1 to about 1, x is greater than 0 to about 0.25, y is in the range of from 0.4 to 0.5, and z is in the range of from 0.25 to 0.5, more preferably m is from 0.15 to 0.7, x is from 0.01 to 0.2, y is from 0.4 to 0.5, and z is from 0.3 to 0.5.

Non-limiting examples of SAPO and ALPO molecular sieves used in the invention include one or a combination of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44 (U.S. Pat. No. 6,162,415), SAPO-47, SAPO-56, ALPO-5, ALPO-11, ALPO-18, ALPO-31, ALPO-34, ALPO-36, ALPO-37, ALPO-46, and metal containing molecular sieves thereof. The more preferred zeolite-type molecular sieves include one or a combination of SAPO-18, SAPO-34, SAPO-35, SAPO-44, SAPO-56, ALPO-18 and ALPO-34, even more preferably one or a combination of SAPO-18, SAPO-34, ALPO-34 and ALPO-18, and metal containing molecular sieves thereof, and most preferably one or a combination of SAPO-34 and ALPO-18, and metal containing molecular sieves thereof.

In an embodiment, the molecular sieve is an intergrowth material having two or more distinct phases of crystalline structures within one molecular sieve composition. In particular, intergrowth molecular sieves are described in the U.S. patent application Ser. No. 09/924,016 filed Aug. 7, 2001 and PCT WO 98/15496 published Apr. 16, 1998, both of which are herein fully incorporated by reference. In another embodiment, the molecular sieve comprises at least one intergrown phase of AEI and CHA framework-types. For example, SAPO-18, ALPO-18 and RUW-18 have an AEI framework-type, and SAPO-34 has a CHA framework-type.

In one embodiment, the molecular sieves used in the invention are combined with one or more other molecular sieves. In another embodiment, the preferred silicoaluminophosphate or aluminophosphate molecular sieves, or a combination thereof, are combined with one more of the following non-limiting examples of molecular sieves described in the following: Beta (U.S. Pat. No. 3,308,069), ZSM-5 (U.S. Pat. Nos. 3,702,886, 4,797,267 and 5,783,321), ZSM-11 (U.S. Pat. No. 3,709,979), ZSM-12 (U.S. Pat. No. 3,832,449), ZSM-12 and ZSM-38 (U.S. Pat. No. 3,948,758), ZSM-22 (U.S. Pat. No. 5,336,478), ZSM-23 (U.S. Pat. No. 4,076,842), ZSM-34 (U.S. Pat. No. 4,086,186), ZSM-35 (U.S. Pat. No. 4,016,245, ZSM-48 (U.S. Pat. No. 4,397,827), ZSM-58 (U.S. Pat. No. 4,698,217), MCM-1 (U.S. Pat. No. 4,639,358), MCM-2 (U.S. Pat. No. 4,673,559), MCM-3 (U.S. Pat. No. 4,632,811), MCM-4 (U.S. Pat. No. 4,664,897), MCM-5 (U.S. Pat. No. 4,639,357), MCM-9 (U.S. Pat. No. 4,880,611), MCM-10 (U.S. Pat. No. 4,623,527), MCM-14 (U.S. Pat. No. 4,619,818), MCM-22 (U.S. Pat. No. 4,954,325), MCM-41 (U.S. Pat. No. 5,098,684), M-41S (U.S. Pat. No. 5,102,643), MCM-48 (U.S. Pat. No. 5,198,203), MCM-49 (U.S. Pat. No. 5,236,575), MCM-56 (U.S. Pat. No. 5,362,697), ALPO-11 (U.S. Pat. No. 4,310,440), titanium aluminosilicates (TASO), TASO-45 (EP-A-0 229,-295), boron silicates (U.S. Pat. No. 4,254,297), titanium aluminophosphates (TAPO) (U.S. Pat. No. 4,500,651), mixtures of ZSM-5 and ZSM-11 (U.S. Pat. No. 4,229,424), ECR-18 (U.S. Pat. No. 5,278,345), SAPO-34 bound ALPO-5 (U.S. Pat. No. 5,972,203), PCT WO 98/57743 published Dec. 23, 1988 (molecular sieve and Fischer-Tropsch), U.S. Pat. No. 6,300,535 (MFI-bound zeolites), and mesoporous molecular sieves (U.S. Pat. Nos. 6,284,696, 5,098,684, 5,102,643 and 5,108,725), which are all herein fully incorporated by reference.

The molecular sieves are made or formulated into catalysts by combining the synthesized molecular sieves with a binder and/or a matrix material to form a molecular sieve catalyst composition or a formulated molecular sieve catalyst composition. This formulated molecular sieve catalyst composition is formed into useful shape and sized particles by conventional techniques such as spray drying, pelletizing, extrusion, and the like.

There are many different binders that are useful in forming the molecular sieve catalyst composition. Non-limiting examples of binders that are useful alone or in combination include various types of hydrated alumina, silicas, and/or other inorganic oxide sol. One preferred alumina containing sol is aluminum chlorhydrol. The inorganic oxide sol acts like glue binding the synthesized molecular sieves and other materials such as the matrix together, particularly after thermal treatment. Upon heating, the inorganic oxide sol, preferably having a low viscosity, is converted into an inorganic oxide matrix component. For example, an alumina sol will convert to an aluminum oxide matrix following heat treatment.

Aluminum chlorhydrol, a hydroxylated aluminum based sol containing a chloride counter ion, has the general formula of $Al_mO_n(OH)_oCl_p \cdot x(H_2O)$ wherein m is 1 to 20, n is 1 to 8, o is 5 to 40, p is 2 to 15, and x is 0 to 30. In one embodiment, the binder is $Al_{13}O_4(OH)_{24}Cl_7 \cdot 12(H_2O)$ as is described in G. M. Wolterman, et al., Stud. Surf. Sci. and Catal., 76, pages 105–144 (1993), which is herein incorporated by reference. In another embodiment, one or more binders are combined with one or more other non-limiting examples of alumina materials such as aluminum oxyhydroxide, γ-alumina, boehmite, diaspore, and transitional aluminas such as α-alumina, β-alumina, γ-alumina, δ-alumina, ε-alumina, κ-alumina, and ρ-alumina, aluminum trihydroxide, such as gibbsite, bayerite, nordstrandite, doyelite, and mixtures thereof.

In another embodiment, the binders are alumina sols, predominantly comprising aluminum oxide, optionally including some silicon. In yet another embodiment, the binders are peptized alumina made by treating alumina hydrates such as pseudobohemite, with an acid, preferably an acid that does not contain a halogen, to prepare sols or aluminum ion solutions. Non-limiting examples of commercially available colloidal alumina sols include Nalco 8676 available from Nalco Chemical Co., Naperville, Ill., and Nyacol available from The PQ Corporation, Valley Forge, Pa.

The molecular sieve, in a preferred embodiment, is combined with one or more matrix material(s). Matrix materials are typically effective in reducing overall catalyst cost, act as thermal sinks assisting in shielding heat from the catalyst composition for example during regeneration, densifying the catalyst composition, increasing catalyst strength such as crush strength and attrition resistance, and to control the rate of conversion in a particular process.

Non-limiting examples of matrix materials include one or more of: rare earth metals, metal oxides including titania, zirconia, magnesia, thoria, beryllia, quartz, silica or sols, and mixtures thereof, for example silica-magnesia, silica-zirconia, silica-titania, silica-alumina and silica-alumina-thoria. In an embodiment, matrix materials are natural clays such as those from the families of montmorillonite and kaolin. These natural clays include sabbentonites and those kaolins known as, for example, Dixie, McNamee, Ga. and Florida clays. Non-limiting examples of other matrix materials include: haloysite, kaolinite, dickite, nacrite, or anauxite. In one embodiment, the matrix material, preferably any of the clays, are subjected to well known modification processes such as calcination and/or acid treatment and/or chemical treatment.

In one preferred embodiment, the matrix material is a clay or a clay-type composition, preferably the clay or clay-type composition having a low iron or titania content, and most preferably the matrix material is kaolin. Kaolin has been found to form a pumpable, high solid content slurry, it has a low fresh surface area, and it packs together easily due to its platelet structure. A preferred average particle size of the matrix material, most preferably kaolin, is from about 0.1 $\mu$m to about 0.6 $\mu$m with a D90 particle size distribution of less than about 1 $\mu$m.

In another embodiment, the weight ratio of the binder to the matrix material used in the formation of the molecular sieve catalyst composition is from 0:1 to 1:15, preferably 1:15 to 1:5, more preferably 1:10 to 1:4, and most preferably 1:6 to 1:5. It has been found that a higher sieve content, lower matrix content, increases the molecular sieve catalyst composition performance, however, lower sieve content, higher matrix material, improves the attrition resistance of the composition.

In another embodiment, the formulated molecular sieve catalyst composition contains from about 1% to about 99%, more preferably from about 5% to about 90%, and most preferably from about 10% to about 80%, by weight of the molecular sieve based on the total weight of the molecular sieve catalyst composition.

In another embodiment, the weight percent of binder in or on the spray dried molecular sieve catalyst composition based on the total weight of the binder, molecular sieve, and matrix material is from about 2% by weight to about 30% by weight, preferably from about 5% by weight to about 20% by weight, and more preferably from about 7% by weight to about 15% by weight.

Once the molecular sieve catalyst composition is formed in a substantially dry or dried state, to further harden and/or activate the formed catalyst composition, a heat treatment such as calcination, at an elevated temperature is usually performed. A conventional calcination environment is air that typically includes a small amount of water vapor. Typical calcination temperatures are in the range from about 400° C. to about 1,000° C., preferably from about 500° C. to about 800° C., and most preferably from about 550° C. to about 700° C., preferably in a calcination environment such as air, nitrogen, helium, flue gas (combustion product lean in oxygen), or any combination thereof.

The process for converting a feedstock, especially a feedstock containing one or more oxygenates, in the presence of a molecular sieve catalyst composition of the invention, is carried out in a reaction process in a reactor, where the process is a fixed bed process, a fluidized bed process (includes a turbulent bed process), preferably a continuous fluidized bed process, and most preferably a continuous high velocity fluidized bed process.

The reaction processes can take place in a variety of catalytic reactors such as hybrid reactors that have a dense bed or fixed bed reaction zones and/or fast fluidized bed reaction zones coupled together, circulating fluidized bed reactors, riser reactors, and the like. Suitable conventional reactor types are described in for example U.S. Pat. No. 4,076,796, U.S. Pat. No. 6,287,522 (dual riser), and *Fluidization Engineering*, D. Kunii and O. Levenspiel, Robert E. Krieger Publishing Company, New York, N.Y. 1977, which are all herein fully incorporated by reference.

The preferred reactor type are riser reactors generally described in *Riser Reactor, Fluidization and Fluid-Particle Systems*, pages 48 to 59, F. A. Zenz and D. F. Othmo, Reinhold Publishing Corporation, New York, 1960, and U.S. Pat. No. 6,166,282 (fast-fluidized bed reactor), and U.S. patent application Ser. No. 09/564,613 filed May 4, 2000 (multiple riser reactor), which are all herein fully incorporated by reference.

In the preferred embodiment, a fluidized bed process or high velocity fluidized bed process includes a reactor system, a regeneration system and a recovery system. The reactor system preferably is a fluid bed reactor system having a first reaction zone within one or more riser reactor(s) and a second reaction zone within at least one disengaging vessel, preferably comprising one or more cyclones. In one embodiment, the one or more riser reactor(s) and disengaging vessel is contained within a single reactor vessel. Fresh feedstock, preferably containing one or more oxygenates, optionally with one or more diluent(s), is fed to the one or more riser reactor(s) in which a zeolite or zeolite-type molecular sieve catalyst composition or coked version thereof is introduced. In one embodiment, the molecular sieve catalyst composition or coked version thereof is contacted with a liquid or gas, or combination thereof, prior to being introduced to the riser reactor(s), preferably the liquid is water or methanol, and the gas is an inert gas such as nitrogen.

In an embodiment, the amount of fresh feedstock fed separately or jointly with a vapor feedstock, to a reactor system is in the range of from 0.1 weight percent to about 85 weight percent, preferably from about 1 weight percent to about 75 weight percent, more preferably from about 5 weight percent to about 65 weight percent based on the total weight of the feedstock including any diluent contained therein. The liquid and vapor feedstocks are preferably the same composition, or contain varying proportions of the same or different feedstock with the same or different diluent.

The feedstock entering the reactor system is preferably converted, partially or fully, in the first reactor zone into a gaseous effluent that enters the disengaging vessel along with a coked molecular sieve catalyst composition. In the preferred embodiment, cyclone(s) within the disengaging vessel are designed to separate the molecular sieve catalyst composition, preferably a coked molecular sieve catalyst composition, from the gaseous effluent containing one or more olefin(s) within the disengaging zone. Cyclones are preferred, however, gravity effects within the disengaging vessel will also separate the catalyst compositions from the gaseous effluent. Other methods for separating the catalyst compositions from the gaseous effluent include the use of plates, caps, elbows, and the like.

In one embodiment of the disengaging system, the disengaging system includes a disengaging vessel, typically a lower portion of the disengaging vessel is a stripping zone. In the stripping zone the coked molecular sieve catalyst composition is contacted with a gas, preferably one or a combination of steam, methane, carbon dioxide, carbon monoxide, hydrogen, or an inert gas such as argon, preferably steam, to recover adsorbed hydrocarbons from the coked molecular sieve catalyst composition that is then introduced to the regeneration system. In another embodiment, the stripping zone is in a separate vessel from the disengaging vessel and the gas is passed at a gas hourly superficial velocity (GHSV) of from 1 $hr^{-1}$ to about 20,000 $hr^{-1}$ based on the volume of gas to volume of coked molecular sieve catalyst composition, preferably at an elevated temperature from 250° C. to about 750° C., preferably from about 350° C. to 650° C., over the coked molecular sieve catalyst composition.

The conversion temperature employed in the conversion process, specifically within the reactor system, is in the range of from about 200° C. to about 1,000° C., preferably from about 250° C. to about 800° C., more preferably from about 250° C. to about 750° C., yet more preferably from about 300° C. to about 650° C., yet even more preferably from about 350° C. to about 600° C. most preferably from about 350° C. to about 550° C.

The conversion pressure employed in the conversion process, specifically within the reactor system, is not critical. The conversion pressure is based on the partial pressure of the feedstock exclusive of any diluent therein. Typically the conversion pressure employed in the process is in the range of from about 0.1 kPaa to about 5 MPaa, preferably from about 5 kPaa to about 1 MPaa, and most preferably from about 20 kPaa to about 500 kPaa.

The weight hourly space velocity (WHSV), particularly in a process for converting a feedstock containing one or more oxygenates in the presence of a molecular sieve catalyst composition within a reaction zone, is defined as the total weight of the feedstock excluding any diluents to the reaction zone per hour per weight of molecular sieve in the molecular sieve catalyst composition in the reaction zone. The WHSV is maintained at a level sufficient to keep the catalyst composition in a fluidized state within a reactor.

Typically, the WHSV ranges from about 1 $hr^{-1}$ to about 5000 $hr^{-1}$ preferably from about 2 $hr^{-1}$ to about 3000 $hr^{-1}$, more preferably from about 5 $hr^{-1}$ to about 1500 $hr^{-1}$, and most preferably from about 10 $hr^{-1}$ to about 1000 $hr^{-1}$. In one preferred embodiment, the WHSV is greater than 20 $hr^{-1}$, preferably the WHSV for conversion of a feedstock containing methanol and dimethyl ether is in the range of from about 20 $hr^{-1}$ to about 300 $hr^{-1}$.

The superficial gas velocity (SGV) of the feedstock including diluent and reaction products within the reactor system is preferably sufficient to fluidize the molecular sieve catalyst composition within a reaction zone in the reactor. The SGV in the process, particularly within the reactor system, more particularly within the riser reactor(s), is at least 0.1 meter per second (m/sec), preferably greater than 0.5 m/sec, more preferably greater than 1 m/sec, even more preferably greater than 2 m/sec, yet even more preferably greater than 3 m/sec, and most preferably greater than 4 m/sec. See for example U.S. patent application Ser. No. 09/708,753 filed Nov. 8, 2000, which is herein incorporated by reference.

In one preferred embodiment of the process for converting an oxygenate to olefin(s) using a silicoaluminophosphate molecular sieve catalyst composition, the process is operated at a WHSV of at least 20 $hr^{-1}$ and a Temperature Corrected Normalized Methane Selectivity (TCNMS) of less than 0.016, preferably less than or equal to 0.01. See for example U.S. Pat. No. 5,952,538, which is herein fully incorporated by reference.

In another embodiment of the processes for converting an oxygenate such as methanol to one or more olefin(s) using a molecular sieve catalyst composition, the WHSV is from 0.01 $hr^{-1}$ to about 100 $hr^{-1}$, at a temperature of from about 350° C. to 550° C., and silica to $Me_2O_3$ (Me is a Group IIIA or VIII element from the Periodic Table of Elements) molar ratio of from 300 to 2500. See for example EP-0 642 485 B1, which is herein fully incorporated by reference.

Other processes for converting an oxygenate such as methanol to one or more olefin(s) using a molecular sieve catalyst composition are described in PCT WO 01/23500 published Apr. 5, 2001 (propane reduction at an average catalyst feedstock exposure of at least 1.0), which is herein incorporated by reference.

According to one embodiment, the conversion of the primary oxygenate, e.g., methanol, is from 90 wt % to 98 wt %. According to another embodiment the conversion of methanol is from 92 wt % to 98 wt %, preferably from 94 wt % to 98 wt %.

According to another embodiment, the conversion of methanol is above 98 wt % to less than 100 wt %. According to another embodiment, the conversion of methanol is from 98.1 wt % to less than 100 wt %; preferably from 98.2 wt % to 99.8 wt %. According to another embodiment, the conversion of methanol is from 98.2 wt % to less than 99.5 wt %; preferably from 98.2 wt % to 99 wt %.

The oxygenate to olefin process forms a substantial amount of water as a by-product. Much of this water can be removed by cooling the olefin stream from the oxygenate reactor to a temperature below the condensation temperature of the water in the stream. Preferably, the temperature of the product stream is cooled to a temperature below the condensation temperature of the oxygenate feed for the oxygenate to olefins process. In certain embodiments, it is desirable to cool the product stream below the condensation temperature of methanol.

A quench column is one type of equipment that is effective in cooling the olefin stream from the olefin to oxygenate reaction process. In a quench column, a quenching fluid is directly contacted with the olefin stream to cool the stream to the desired condensation temperature. Condensation produces the condensed water containing stream, which is also referred to as a heavy bottoms stream. The olefin portion of the olefin product stream remains a vapor, and exits the quench column as an overhead vapor stream. The overhead vapor stream is rich in olefin product, and can also contain some oxygenated hydrocarbon by-products as well as water.

In one embodiment, the quenching fluid is a recycle stream of the condensed water containing, heavy bottoms stream of the quench column. This water containing stream is desirably cooled, e.g., by a heat exchanger, and injected back into the quench column. It is preferred in this embodiment to not inject cooling medium from an outside source into the quench column, although it may be desirable to do so in other separation equipment down stream of the quench column.

In one particular embodiment of the invention, the quenched olefin stream is further processed by compression, preferably multi-staged compression. Two, three, four or more stages can be used, with two or three stages being preferred.

In another embodiment of the invention, the olefin stream is compressed to a pressure that is greater than that at which the oxygenate to olefin reaction process is carried out. Preferably, the olefin stream is compressed to a pressure of at least about 30 psia (207 kPa), more preferably at least about 50 psia (345 kPa), most preferably at least about 100 psia (689 kPa). High pressure ranges are particularly preferred, with the upper limit being a practical one based on cost of design and ease of operation. Practical high pressure limits are generally considered to be up to about 5,000 psia (34,450 kPa), with lower limits of about 1,000 psia (6,895 kPa), about 750 psia (5171 kPa), and about 500 psia (3447 kPa) being increasingly preferred.

In one embodiment of the invention, the separation of the acetaldehyde from the olefin stream takes place in a distillation type of column and the operation pressure of the column is held so that the second fraction or bottoms portion of the column is at a relatively low temperature so as to limit equipment fouling. This second fraction will contain a majority of the $C_4+$ olefin components; and in this embodiment, it is preferred that the second fraction have an average temperature of not greater than about 300° F. (149° C.), more preferably not greater than about 275° F. (135° C.), and most preferably not greater than about 250° F. (121° C.).

In this invention it is desirable to obtain high concentrations of ethylene and propylene from an olefin stream containing acetaldehyde. In one embodiment, the acetaldehyde is separated from the ethylene and propylene in the olefin stream. In this embodiment the ethylene and propylene are recovered in a first fraction, and the acetaldehyde is recovered in a second fraction. Typically, the first fraction will be the overhead or side fraction of a distillation column, and the second fraction will be a bottoms fraction or additional side fraction of a distillation column.

In one embodiment of the invention, a majority of the ethylene and propylene in the provided olefin stream will be separated in a first fraction and a majority of the acetaldehyde in the provided olefin stream will be separated in a second fraction. Preferably, the first fraction will contain at least about 75% of the ethylene and propylene in the provided olefin stream, more preferably at least about 85%, and most preferably at least about 95%.

In another embodiment, at least about 75% of the acetaldehyde in the provided olefin stream will be separated out in the second fraction. Preferably, at least about 85% of the acetaldehyde in the provided olefin stream will be separated out in the second fraction, more preferably at least about 95%, and most preferably at least about 99%.

This invention is particularly advantageous for acid gas treating the ethylene and propylene streams contained in the first fraction to remove entrained acid gases such as $CO_2$ which may also be present in such fraction. The advantage is that in this invention the separated ethylene and propylene streams will contain relatively few hydrocarbon components that cause fouling problems in such acid gas treatment systems.

Solid or liquid acid gas treatment systems can be used in this invention. In either system, the acid gas is removed from the ethylene and/or propylene stream in the first fraction by contacting the first fraction with an acid gas absorbent or adsorbent. Examples of such absorbents or adsorbents include amines, potassium carbonate, caustic, alumina, molecular sieves, and membranes, particularly membranes formed of polysulfone, polyimid, polyamide, glassy polymer and cellulose acetate. Solutions containing amines and caustic compounds are preferred, with caustic compounds being more preferred.

Aqueous amine solutions which are useful in this invention can contain any amine compound or compounds suitable for acid gas absorption. Examples include alkanolamines, such as triethanolamine (TEA); methyldiethanolamine (MDEA); diethanolamine (DEA); monoethanolamine (MEA); diisopropanolamine (DIPA); and hydroxyaminoethyl ether (DGA). Effective concentrations can range from about 0.5 to about 8 moles of amine per liter of aqueous solution.

Piperazine and/or monomethylethanolamine (MMEA) can be added to aqueous amine solutions to enhance their absorption capabilities. These additives can be included in the aqueous solution at a concentration of from about 0.04 to about 2 moles per liter of aqueous solution.

Caustic compounds which can be used in this invention are alkaline compounds which are effective in removing acid gas from an olefin stream. Examples of such alkaline compounds include sodium hydroxide and potassium hydroxide.

Following acid gas treating, it is desirable to remove additionally entrained material in the treated ethylene and/or propylene using a water wash. Conventional equipment can be used. It is desirable, however, to further remove additional water from the separated ethylene and/or propylene streams.

In one embodiment of this invention, the ethylene and propylene in the first fraction is water washed, i.e., contacted with a water stream, prior to acid gas treating. This contacting is particularly advantageous when water absorbent is added to the oxygenate separation vessel, as water absorbent may carry over into the first or overhead fraction. Water washing would then be conducted to remove a substantial portion of water absorbent carry over prior to acid gas treating.

This invention further includes an optional drying embodiment. In this embodiment, a solid or liquid drying system can be used to remove water and/or additional oxygenated hydrocarbon from the first fraction.

In the solid drying system, the ethylene and/or propylene having been separated in a first fraction, and optionally acid gas treated and water washed, is contacted with a solid adsorbent to further remove water and oxygenated hydrocarbon to very low levels. Typically, the adsorption process is carried out in one or more fixed beds containing a suitable solid adsorbent.

Adsorption is useful for removing low concentrations of water and oxygenated hydrocarbons, and for removing oxygenated hydrocarbons that may not normally be removed by using other treatment systems. Preferably, an adsorbent system used as part of this invention has multiple adsorbent beds. Multiple beds allow for continuous separation without the need for shutting down the process to regenerate the solid adsorbent. For example, in a three bed system typically one bed is on-line, one bed is regenerated off-line, and a third bed is on stand-by.

The specific adsorbent solid or solids used in the adsorbent beds depends on the types of contaminants being removed. Examples of solid adsorbents for removing water and various polar organic compounds, such as oxygenated hydrocarbons and absorbent liquids, include aluminas, silica, 3A molecular sieves, 4A molecular sieves, and alumino-silicates. Beds containing mixtures of these sieves or multiple beds having different adsorbent solids can be used to remove water, as well as a variety of oxygenated hydrocarbons.

In this invention, one or more adsorption beds can be arranged in series or parallel. In one example of a series arrangement, a first bed is used to remove the smallest and most polar molecules which are the easiest to remove. Subsequent beds for removing larger less polar oxygenated species are next in series. As a specific example of one type of arrangement, water is first selectively removed using a 3A molecular sieve. This bed is then followed by one or more beds containing one or more less selective adsorbents such as a larger pore molecular sieve e.g. 13× and/or a high surface area active alumina such as Selexorb CD (Alcoa tradename).

In another embodiment, the first bed is a 3.6A molecular sieve capable of selectively removing both water and methanol. This bed can then be followed by one or more 13× or active alumina beds as described above.

The adsorbent beds can be operated at ambient temperature or at elevated temperature as required, and with either upward or downward flow. Regeneration of the adsorbent materials can be carried out by conventional methods including treatment with a stream of a dry inert gas such as nitrogen at elevated temperature.

In the liquid drying system, a water absorbent is used to remove water from the first fraction. The water absorbent can be any liquid effective in removing water from an olefin stream. Preferably, the water absorbent is the same as that previously described.

Preferably the olefin from the adsorption beds contains less than about 100 wppm water, more preferably less than about 10 wppm, and most preferably less than 1 wppm. Preferably less than about 10 wppm oxygenated hydrocarbons are present in the stream leaving the adsorption beds, more preferably less than about 5 wppm, and most preferably less than about 1 wppm.

The ethylene and propylene streams treated and separated according to this invention can be polymerized to form plastic compositions, e.g., polyolefins, particularly polyethylene and polypropylene. Any conventional process for forming polyethylene or polypropylene can be used. Catalytic processes are preferred. Particularly preferred are metallocene, Ziegler/Natta, aluminum oxide and acid catalytic systems. See, for example, U.S. Pat. Nos. 3,258,455; 3,305,538; 3,364,190; 5,892,079; 4,659,685; 4,076,698; 3,645,992; 4,302,565; and 4,243,691, the catalyst and process descriptions of each being expressly incorporated herein by reference. In general, these methods involve contacting the ethylene or propylene product with a polyolefin-forming catalyst at a pressure and temperature effective to form the polyolefin product.

In one embodiment of this invention, the ethylene or propylene product is contacted with a metallocene catalyst to form a polyolefin. Desirably, the polyolefin forming process is carried out at a temperature ranging between about 50° C. and about 320° C. The reaction can be carried out at low, medium or high pressure, being anywhere within the range of about 1 bar to about 3200 bar. For processes carried out in solution, an inert diluent can be used. In this type of operation, it is desirable that the pressure be at a range of from about 10 bar to about 150 bar, and preferably at a temperature range of from about 120° C. to about 250° C. For gas phase processes, it is preferred that the temperature generally be within a range of about 60° C. to 120° C., and that the operating pressure be from about 5 bar to about 50 bar.

In addition to polyolefins, numerous other olefin derivatives may be formed from the ethylene, propylene and $C_4+$ olefins, particularly butylene, separated according to this invention. The olefins separated according to this invention can also be used in the manufacture of such compounds as aldehydes, acids such as $C_2$–$C_{13}$ mono carboxylic acids, alcohols such as $C_2$–$C_{12}$ mono alcohols, esters made from the $C_2$–$C_{12}$ mono carboxylic acids and the $C_2$–$C_{12}$ mono alcohols, linear alpha olefins, vinyl acetate, ethylene dicholoride and vinyl chloride, ethylbenzene, ethylene oxide, cumene, acrolein, allyl chloride, propylene oxide, acrylic acid, ethylene-propylene rubbers, and acrylonitrile, and trimers and dimers of ethylene and propylene. The $C_4+$ olefins, butylene in particular, are particularly suited for the manufacture of aldehydes, acids, alcohols, esters made from $C_5$–$C_{13}$ mono carboxylic acids and $C_5$–$C_{13}$ mono alcohols and linear alpha olefins.

One example of separating an acetaldehyde and $C_4+$ stream from ethylene and/or propylene and treating the ethylene and/or propylene is shown in the FIGURE. This example is but one way of providing an ethylene and propylene stream substantially depleted of acetaldehyde, water and $C_4+$ olefins. The common factor in this invention, however, is that acetaldehyde and $C_4+$ olefins are substantially removed from the ethylene and/or propylene containing stream prior to acid gas treatment. This means that both ethylene and propylene can be recovered in the overhead stream following removal of the acetaldehyde and $C_4+$ olefins or that propylene can also be removed along with the acetaldehyde and $C_4+$ olefins in the bottoms stream. When ethylene and propylene are both recovered in the overhead stream, the components can be treated, e.g., caustic wash treated, together or separated and treated separately.

The FIGURE shows one embodiment in which the olefin to be treated is made in an oxygenate to olefin reaction system. In the FIGURE, methanol is sent through a line 10 to an oxygenate to olefin reactor where the methanol is converted to an olefin stream comprising methane, ethylene, propylene, acetaldehyde, $C_4+$ olefins, water and other hydrocarbon components. The olefin stream is sent through a line 14 to a quench tower 16 where the olefin is cooled and water and other condensable components are condensed.

The condensed components, which comprise a substantial amount of water, are withdrawn from the quench tower 16 through a bottoms line 18. A portion of the condensed components are recycled through a line 20 back to the top of the quench tower 16. The line 20 contains a cooling unit, e.g., heat exchanger, (not shown) to further cool the condensed components so as to provide a cooling medium to further cool the components in quench tower 16.

Olefin vapor leaves the top portion of quench tower 16 through a line 22. The olefin vapor is compressed in compressor 24 and the compressed olefin is passed through a line 26 to an distillation column 28. Methanol is fed to an upper portion of the distillation column 28 as an extractant to extract acetaldehyde along with the $C_4+$ olefins. The acetaldehyde, $C_4+$ olefins and methanol extractant leave the distillation column 28 through a lower, bottoms line 30. A portion of the material in the bottoms line 30 is recycled through a line 32 back to the distillation column 28. The line 32 contains a heating system, e.g., heat exchanger, (not shown) which provides heat to the distillation column 28.

Olefin vapor comprising the methane, ethylene, propylene and other lower boiling point material leaves the extractive distillation column 28 through a line 34, and is sent to a caustic wash column 36. A caustic solution is sent through a line 38 to the top portion of the caustic wash column 36 to remove $CO_2$, which is also entrained in the olefin vapor. Spent caustic leaves the caustic wash column 36 through a line 40.

Olefin vapor which has been treated in the caustic wash column 36, leaves through a line 42, and is sent to a dryer system 44, e.g., adsorbent system. The dryer system 44 removes a substantial portion of any water and oxygenated hydrocarbons which still remain in the treated olefin vapor stream. The dried olefin vapor stream is then passed through a line 46 to a separator, e.g., distillation column, to separate methane and lighter boiling point components through a line 50, ethylene through a line 52, and propylene through a line 54.

Having now fully described this invention, it will be appreciated by those skilled in the art that the invention can be performed within a wide range of parameters within what is claimed, without departing from the spirit and scope of the invention.

What is claimed is:

1. A method of treating an ethylene and/or propylene containing stream, comprising:
   providing an olefin stream containing ethylene, propylene, $C_4+$ olefins and acetaldehyde;
   separating the olefin stream into a first fraction and a second fraction, wherein the first fraction comprises at least a majority of the ethylene and/or propylene present in the olefin stream, and the second fraction comprises at least a majority of the $C_4+$ olefins and acetaldehyde present in the olefin stream; and
   acid gas treating the first fraction.

2. The method of claim 1, wherein the provided olefin stream further comprises $CO_2$, and the first fraction further contains at least a majority of the $CO_2$ in the provided olefin stream.

3. The method of claim 2, wherein acid gas treating the first fraction comprises contacting the first fraction with caustic.

4. The method of claim 1, wherein the second fraction is comprised of at least 5 wt % $C_4+$ olefin, based on the total weight of the second fraction.

5. The method of claim 1, wherein the olefin stream is separated by distillation.

6. The method of claim 2, wherein the distillation is extractive distillation using an extractant.

7. The method of claim 6, wherein the extractant is a polar composition having an average boiling point of at least 100° F. (38° C.) at 1 atm.

8. The method of claim 7, wherein the extractant is methanol.

9. The method of claim 1, wherein the first fraction comprises at least a majority of the ethylene present in the olefin stream, and the second fraction comprises at least a majority of the propylene present in the olefin stream.

10. The method of claim 1, wherein the first fraction comprises at least a majority of the ethylene and propylene present in the olefin stream.

11. The method of claim 1, wherein the second fraction comprises at least 1,000 wppm acetaldehyde.

12. The method of claim 1, wherein the provided olefin stream further contains propane, and the first fraction comprises at least a majority of the ethylene, propylene and propane present in the olefin stream.

13. The method of claim 1, wherein the provided olefin stream further contains propane, the first fraction comprises at least a majority of the ethylene and propylene present in the olefin stream, and the second fraction further comprises at least a majority of the propane present in the olefin stream.

14. A method of treating an ethylene and/or propylene containing stream made from an oxygenate to olefin process comprising:
    contacting oxygenate with a molecular sieve catalyst to form an olefin stream comprising ethylene, propylene, and acetaldehyde;
    separating the olefin stream into a first fraction and a second fraction, wherein the first fraction comprises at least a majority of the ethylene and/or propylene present in the olefin stream, and the second fraction comprises at least a majority of the acetaldehyde present in the olefin stream; and
    acid gas treating the first fraction.

15. The method of claim 14, wherein the olefin stream further comprises $CO_2$, and the first fraction further contains at least a majority of the $CO_2$ in the provided olefin stream.

16. The method of claim 15, wherein acid gas treating the first fraction comprises contacting the first fraction with caustic.

17. The method of claim 14, wherein the olefin stream further comprises $C_4+$ olefins, and the second fraction further comprises at least 5 wt % $C_4+$ olefin, based on the total weight of the second fraction.

18. The method of claim 14, wherein the olefin stream is separated by distillation.

19. The method of claim 18, wherein the distillation is extractive distillation using an extractant.

20. The method of claim 19, wherein the extractant is a polar composition having an average boiling point of at least 100° F. (38° C.) at 1 atm.

21. The method of claim 20, wherein the extractant is methanol.

22. The method of claim 14, wherein the first fraction comprises at least a majority of the ethylene present in the olefin stream, and the second fraction comprises at least a majority of the propylene present in the olefin stream.

23. The method of claim 14, wherein the first fraction comprises at least a majority of the ethylene and propylene present in the olefin stream.

24. The method of claim 14, wherein the second fraction comprises at least 1,000 wppm acetaldehyde.

25. The method of claim 14, wherein the olefin stream further contains propane, and the first fraction comprises at least a majority of the ethylene, propylene and propane present in the olefin stream.

26. The method of claim 14, wherein the olefin stream further contains propane, the first fraction comprises at least a majority of the ethylene and propylene present in the olefin stream, and the second fraction comprises at least a majority of the propane present in the olefin stream.

27. A method of treating an ethylene containing stream, comprising:
    providing an olefin stream containing ethylene, propylene, $C_4+$ olefins and acetaldehyde;
    separating the olefin stream into a first fraction and a second fraction, wherein the first fraction comprises at least a majority of the ethylene present in the olefin stream and the second fraction comprises at least a majority of the propylene, $C_4+$ olefin and acetaldehyde present in the olefin stream; and
    acid gas treating the first fraction.

28. The method of claim 27, wherein the provided olefin stream further comprises $CO_2$, and the first fraction further contains at least a majority of the $CO_2$ in the provided olefin stream.

29. The method of claim 28, wherein acid gas treating the first fraction comprises contacting the first fraction with caustic.

30. The method of claim 29, wherein the olefin stream is separated by distillation.

31. The method of claim 30, wherein the distillation is extractive distillation using an extractant.

32. The method of claim 31, wherein the extractant is a polar composition having an average boiling point of at least 100° F. (38° C.) at 1 atm.

33. The method of claim 32, wherein the extractant is methanol.

34. The method of claim 27, wherein ethylene in the first fraction is polymerized to form polyethylene.

35. A method of treating an ethylene and propylene containing stream comprising:
   providing an olefin stream containing ethylene, propylene, $C_4+$ olefins and acetaldehyde;
   separating the olefin stream into an first fraction and a second fraction, wherein the first fraction comprises at least a majority of the ethylene and propylene present in the olefin stream, and the second fraction comprises at least a majority of the $C_4+$ olefins and acetaldehyde present in the olefin stream; and
   acid gas treating the first fraction.

36. The method of claim 35, wherein the provided olefin stream further comprises $CO_2$, and the first fraction further contains at least a majority of the $CO_2$ in the provided olefin stream.

37. The method of claim 36, wherein acid gas treating the first fraction comprises contacting the first fraction with caustic.

38. The method of claim 35, wherein the olefin stream is separated by distillation.

39. The method of claim 38, wherein the distillation is extractive distillation using an extractant.

40. The method of claim 39, wherein the extractant is a polar composition having an average boiling point of at least 100° F. (38° C.) at 1 atm.

41. The method of claim 40, wherein the extractant is methanol.

42. The method of claim 35, wherein the ethylene and propylene in the first fraction are separated before or after acid gas treatment, and polymerized to form polyethylene and polypropylene.

43. The method of claim 35, wherein the second fraction comprises at least 1,000 wppm acetaldehyde.

44. The method of claim 35, wherein the provided olefin stream further contains propane, and the first fraction further comprises at least a majority of propane present in the olefin stream.

45. The method of claim 35, wherein the provided olefin stream further contains propane, and the second fraction further comprises at least a majority of the propane present in the olefin stream.

* * * * *